United States Patent [19]

Bumol et al.

[11] Patent Number: 5,196,324
[45] Date of Patent: Mar. 23, 1993

[54] MONOCLONAL ANTIBODIES REACTIVE WITH A HUMAN ATHEROMA ASSOCIATED ANTIGEN

[75] Inventors: Thomas F. Bumol, Carmel, Ind.; Leslie M. McEvoy, Mountain View, Calif.

[73] Assignee: Eli Lilly and Company, Indianapolis, Ind.

[21] Appl. No.: 599,549

[22] Filed: Oct. 17, 1990

Related U.S. Application Data

[63] Continuation-in-part of Ser. No. 451,399, Dec. 15, 1989.

[51] Int. Cl.$^5$ .................. C12P 21/08; C07K 3/18; C12N 15/02; A61K 39/00
[52] U.S. Cl. ....................... 435/70.21; 530/422; 530/412; 435/172.2; 424/88
[58] Field of Search .............. 424/88; 435/7.2, 172.2, 435/70.21; 530/412, 422

[56] References Cited

U.S. PATENT DOCUMENTS

| | | | |
|---|---|---|---|
| 4,376,110 | 3/1983 | David et al. | 436/513 |
| 4,632,901 | 12/1936 | Valkirs et al. | 435/5 |
| 4,727,019 | 2/1988 | Valkirs et al. | 435/5 |
| 4,885,256 | 12/1989 | Alving et al. | 436/518 |
| 4,945,040 | 7/1990 | Fless et al. | 435/7 |

FOREIGN PATENT DOCUMENTS 0189688 8/1986 European Pat. Off. .
0293524 12/1988 European Pat. Off. .
0334076 10/1989 European Pat. Off. .

OTHER PUBLICATIONS

Palinski et al., 1989, Proc. Natl. Acad. Sci. USA, 86:1372–1376.
Zaidi et al, 1982, Chemical Abstracts, 96(23):19609/e.
Bauer et al., 1982 Atherosclerosis, 44:153–160.
Palinski et al., 1990, Artheriosclerosis, 10(3):325–335.
Gonen et al., 1987, Atherosclerosis 65:265–272.
Haberland et al., 1988, Science 241:215–218.
Palinski et al., Abstract No. 0055 from the 61st Scientific Session of the American Heart Association meeting of Nov. 14–17, 1988 in Washington, D.C.
Palinski et al., Abstract No. 424 from the FASEB Journal 2(4) Mar. 15, 1988, presented at the Federation of American Societies for Experimental Biology on May 1–5, 1988 in Las Vegas, Nevada.
Kimura et al., 1986, Virchows Arch A 410:159–164.
Boyd et al., 1989, Am. J. Pathology 135:815–825.
Chait et al., 1989, Abstract No. 0645 from the 62nd Scientific Session of the American Heart Association meeting of Nov. 13–16 in New Orleans, Louisiana.
Steinbrecher et al., 1984, J. Lipid. Res. 25:1109–1116.

Primary Examiner—Y. Christina Chan
Assistant Examiner—Susan L. Futrovsky
Attorney, Agent, or Firm—Douglas K. Norman; Leroy Whitaker

[57] ABSTRACT

The present invention relates to a naturally occurring, minimally modified LDL antigen which is present in human atherosclerotic lesions as well as in the serum of a high percentage of patients with coronary artery disease. The invention also comprises antibodies reactive with the antigen, hybridoma cell lines that produce the antibodies of the inveniton, and methods for using the antibodies in the diagnosis and treatment of atherosclerotic disease.

4 Claims, 5 Drawing Sheets

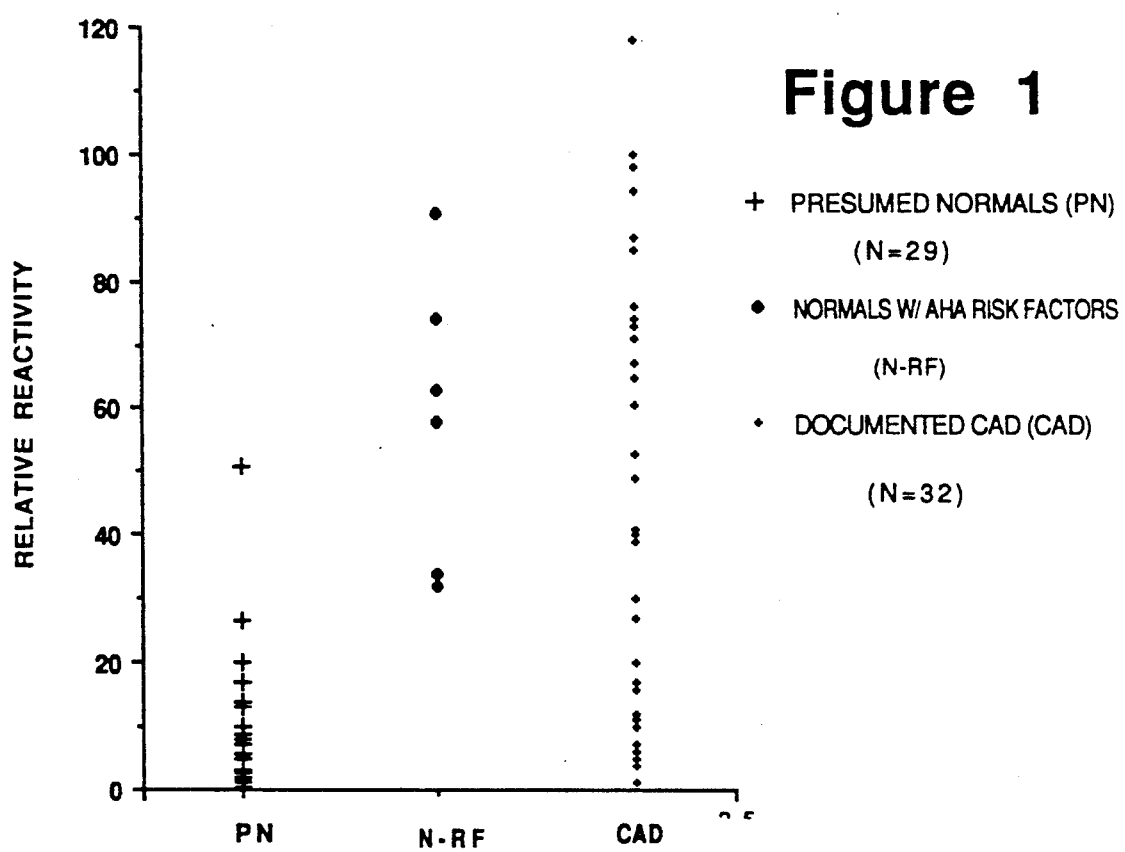

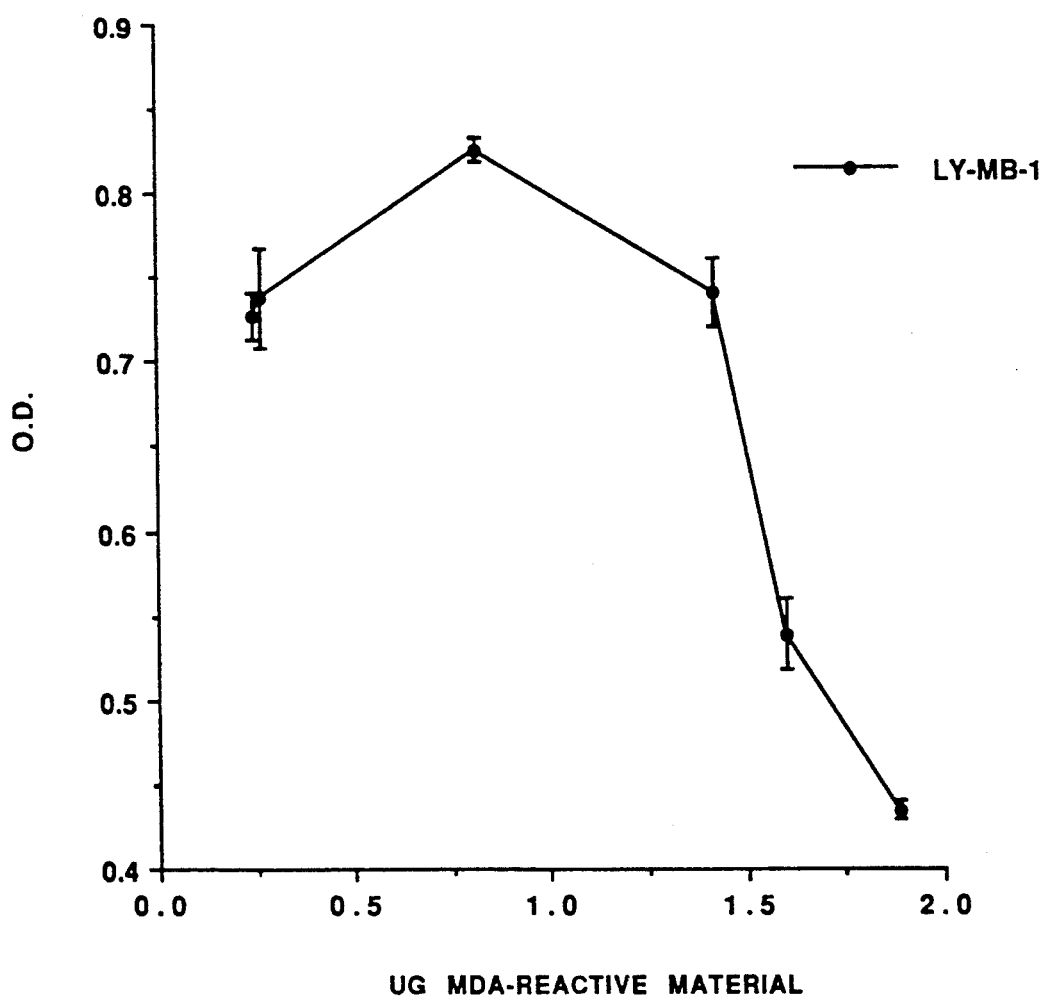

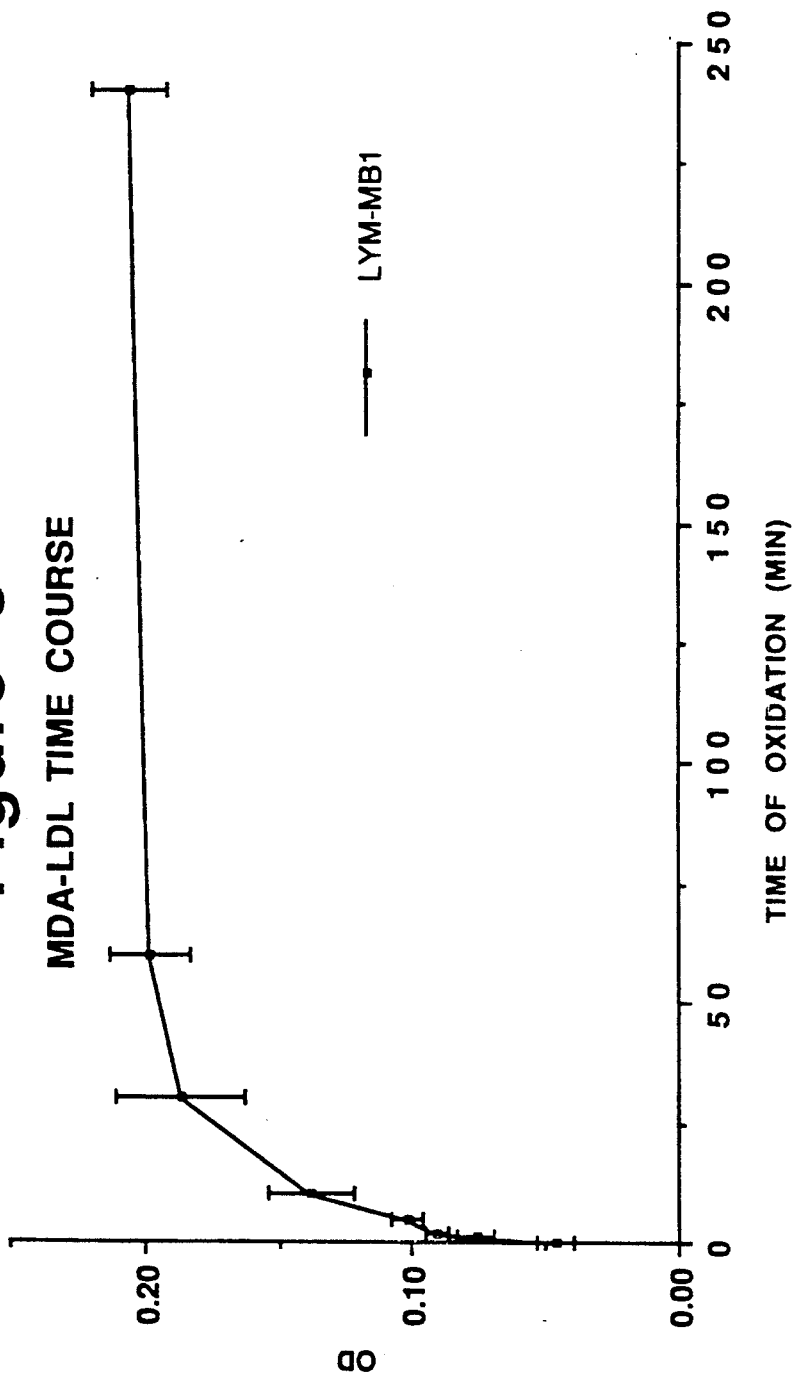

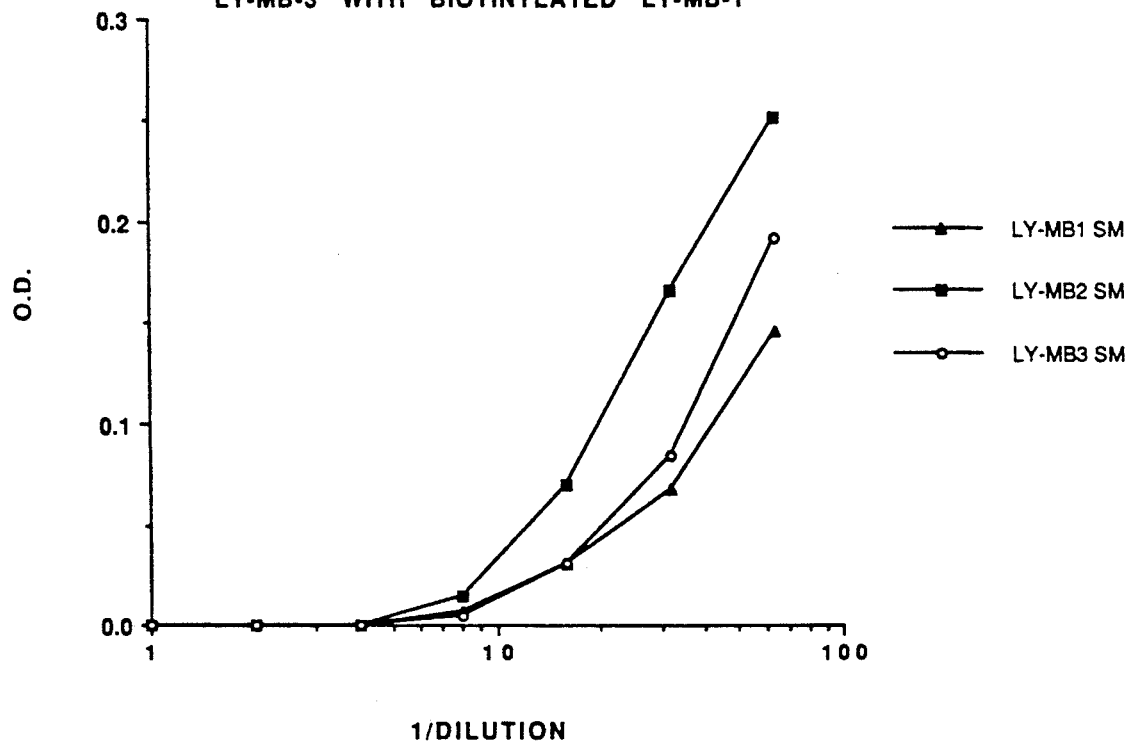

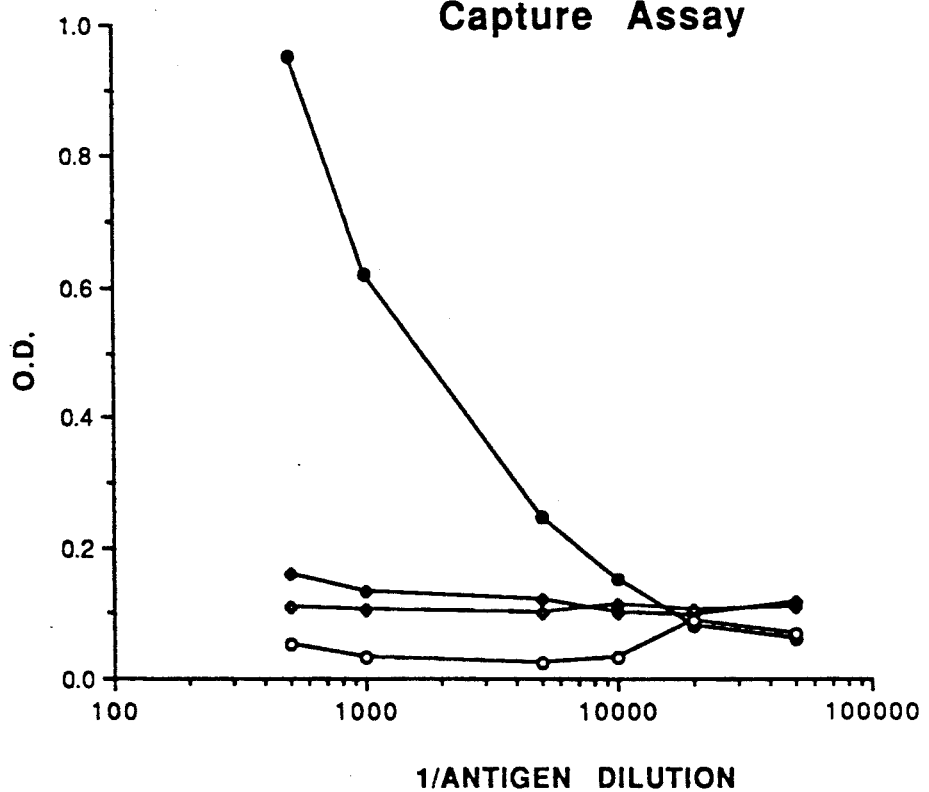

MONOCLONAL ANTIBODIES REACTIVE WITH A HUMAN ATHEROMA ASSOCIATED ANTIGEN

This application is a continuation-in-part of copending U.S. patent application Ser. No. 07/451,399, filed Dec. 15, 1989, pending.

SUMMARY OF THE INVENTION

Atherosclerosis and its complications, such as myocardial infarction, stroke and peripheral vascular disease, are a major cause of death in the United States and Western Europe. The first type of lesion seen, called fatty streaks, are grossly visible, raised, yellow areas which consist of subendothelial foam cells (lipid-filled cells derived from macrophages and smooth muscle cells) and some leukocytes. The second type of atherosclerotic lesion, which causes narrowing of the vessel and predisposes the vessel to thrombosis and calcification, is the fibro-fatty plaque. A typical plaque consists of a fibrous cap composed of smooth muscle cells, a few leukocytes and dense extracellular material. A cellular area beneath the cap generally consists of macrophages, foam cells, smooth muscle cells, leukocytes, cellular debris, extracellular lipid, cholesterol crystals and calcium deposits. The cholesterol that accumulates in both of these types of atherosclerotic lesions originates primarily in plasma lipoproteins, predominantly low density lipoprotein (LDL).

Elevated levels of plasma LDL are associated with accelerated atherosclerosis. There is growing evidence supporting the hypothesis that oxidative modification of LDL renders it more atherogenic. Uptake of native LDL does not appear to be responsible for LDL accumulation in the lesion; however, when native LDL is modified, by oxidation for example, it is recognized and taken up by the scavenger receptor, a specific receptor distinct from the LDL receptor. The scavenger receptor recognizes chemically modified LDL including acetylated LDL, malondialdehyde-conjugated LDL, as well as LDL modified by cultured endothelial cells, monocytes and smooth muscle cells. This receptor is found on monocyte/macrophages, endothelial cells and smooth muscle cells. Thus modified LDL is a key element in plaque formation and/or progression. Markers or methods to detect modified LDL would be valuable diagnostic and/or prognostic tools.

The present invention is directed to a naturally occurring, minimally modified LDL molecule which is present in human atherosclerotic plaque as well as in the plasma and serum of a high percentage of patients with advanced coronary artery disease. Oxidative modification of LDL generates a new epitope on the LDL core protein, apo B100 which is specifically recognized by macrophage receptors. The antibodies of the invention also recognize a neoepitope generated upon modification of LDL as demonstrated by western blotting and enzyme linked immunoassay (ELISA). These antibodies do not react with native LDL but do react with malondialdehyde-conjugated LDL and acetylated LDL.

The invention is also directed to hybridoma cell lines that produce antibodies which are reactive with the atheroma-associated antigen set forth above. The invention is also directed to the antibodies which react with the atheroma-associated neoepitope and which are produced by the hybridoma cell lines. The invention further is directed to a method of detecting the presence of an atheroma-associated neoepitope in a sample, as well as using the atheroma-associated neoepitope reactive antibodies for the diagnosis and therapy of atherosclerotic disease. The invention is also directed to specific methods for preparing immunogen comprising the atheroma-associated antigen of the present invention.

For purposes of the present invention, as disclosed and claimed herein, the following terms are as defined below.

Apolipoprotein $B_{100}$ (apo $B_{100}$)—the high molecular weight protein found in LDL. Apolipoprotein $B_{100}$ contains the recognition site for binding of LDL to its receptor.

Low density lipoprotein (LDL)—lipid-protein complexes consisting of free and esterified cholesterol, phospholipids, triacylglycerol and apolipoprotein B. LDL is the major cholesterol-transporting vehicle in plasma.

MB001—a naturally occurring, minimally modified LDL molecule which is present in human atherosclerotic plaque as well as in the plasma and serum of a high percentage of patients with coronary artery disease and which is recognized by the monoclonal antibodies secreted by hybridoma cell lines P5C11 (LY-MB1) (ATCC HB10262), P1E4 (LY-MB2) (ATCC HB10263) P2E4 (LY-MB3) (ATCC HB10264) and MF2:2.5A4 (LY-MB5) (ATCC HB10535).

Lp(a)—a lipoprotein (a) molecule which contains one molecule of apolipoprotein $B_{100}$ plus one or two molecules of apolipoprotein (a) (apo(a)).

BRIEF DESCRIPTION OF THE FIGURES

FIG. 1—A chart showing the relative reactivity of the serum of a group of individuals with the monoclonal antibodies of the present invention. The large crosses represent individuals who are presumed normal (PN). The black squares represent individuals with American Heart Association-recognized risk factors for coronary artery disease (N-RF). The small crosses represent individuals with documented coronary artery disease (CAD).

FIG. 2—A graph representing the relative reactivity of monoclonal antibody P5C11 (LY-MB1) with copper oxidized LDL.

FIG. 3—A graph representing the reactivity of monoclonal antibody P5C11 (LY-MB1) with malondialdehyde (MDA)-oxidized LDL over a time course of oxidation.

FIG. 4—A graph demonstrating the antigenbinding competition between monoclonal antibodies P5C11 (LY-MB1), P1E4 (LY-MB2) and P2E4 (LY-MB3) from spent media (SM).

FIG. 5—A graph demonstrating the ability of monoclonal antibody P5C11 (LY-MB1) to capture the MB001 antigen from various dilutions of plasma. Black circles represent P5C11 bound to the solid support at 10 $\mu$g/ml. The black diamonds represent bound monoclonal antibody 9.2.27 as a negative control. Open characters represent the same concentration of antibody, but no antigen added as a negative control.

DETAILED DESCRIPTION OF THE INVENTION

The present invention comprises hybridoma cell lines that produce antibodies reactive with the atheroma associated antigen MB001. The antibodies produced by these hybridomas, as well as the purified antigen, are also important aspects of the invention.

The antigen, designated MB001, is a naturally-occurring, minimally modified LDL molecule. The MB001 antigen is present in human atherosclerotic lesions and is immunoreactive with monoclonal antibodies produced by hybridoma cell lines P1E4, P2E4, P5C11 and MF2:2.5A4. The antigen is found both within the atherosclerotic lesion as well as in the serum and plasma of a majority individuals with documented coronary artery disease. The antigen is proteinaceous in structure in that treatment with pepsin and trypsin and boiling diminish its reactivity with the antibodies produced by hybridoma cell lines P5C11 (LY-MB1), P1E4 (LY-MB2), P2E4 (LY-MB3) and MF2:2.5A4 (LY-MB5).

The presence of modified LDL in the blood, serum or plasma has never been described and it is generally accepted that the LDL particle is protected from oxidation in whole blood or plasma by circulating endogenous antioxidants such as vitamin E and $\beta$-carotene. Since the cells found in atherosclerotic lesions; endothelial cells, smooth muscle cells and macrophages, are all capable of modifying LDL so that it is recognized by the scavenger receptor, it is thought that LDL is modified in the vessel wall where it is rapidly taken up by local macrophages and smooth muscle cells. The monoclonal antibodies of this invention react with modified LDL in serum and/or plasma indicating that epitopes consistent with modified- or minimally-modified LDL are found in the circulation and that it is possible that at least minimal modification of LDL does occur in the blood, or that LDL is modified at some location other than the site of a lesion and released into the blood, or that LDL is modified in the vessel wall and is released back into the circulation.

Studies with antisera to Lp(a) in combination with the antibodies of this invention have demonstrated that the Lp(a) molecular complex found in plasma or serum contains epitope(s) which are consistent with modified or minimally-modified LDL. As Lp(a) is a molecular complex of one molecule of apolipoprotein $B_{100}$ plus one or two molecules of apolipoprotein(a), these data suggest that the apolipoprotein $B_{100}$ molecule is modified or minimally-modified in the biosynthesis of the Lp(a) complex. As modified lipoproteins such as modified or minimally-modified apo $B_{100}$ are implicated in atherogenesis, these observations suggest a mechanism by which the Lp(a) complex can be atherogenic.

LDL molecules from human subjects not significantly reactive with antisera to Lp(a) can be made reactive to the antibodies of this invention by a variety of methods described below which can modify or minimally-modify the apo $B_{100}$ molecule. These data suggest that the epitope(s) recognized by the antibodies of this invention are inherent in the apo $B_{100}$ molecule whether it is in the LDL particle or participates in the Lp(a) complex.

Hybridoma cell lines of the present invention can be prepared using salt/detergent extracts of human atherosclerotic lesions or antigen isolated from serum or plasma as immunogenic material for activation of immunologically relevant lymph cells. Lymph cells are then immortalized by fusion with mouse myeloma cells. The hybrid cells, called hybridomas, or hybridoma cell lines, resulting from the fusion are then selected and screened for reactivity with the MB001 antigen presented in salt/detergent extracts from human atherosclerotic lesions, or from serum of individuals with documented peripheral and coronary artery disease, or LDL modified in vitro.

The broad distribution of the MB001 antigen in atherosclerotic lesions and in serum illustrates the diagnostic and therapeutic methods of the invention. Pathology samples of fresh human atherosclerotic lesions and normal arterial tissue were evaluated to demonstrate the ability of the MB001-reactive antibodies of the present invention to distinguish between normal and diseased tissue. Human serum was also tested to illustrate that the MB001-reactive antibodies are useful to identify individuals suffering from peripheral or coronary artery disease. Details of these experiments are provided in the following Examples.

The hybridoma technology originally described by Kohler and Milstein, 1975, Nature 256:495–497 can be used to prepare hybridoma cell lines whose secretory products, monoclonal antibodies, are reactive with the MB001 antigen. A general method of preparing these hybridoma cell lines of the invention is described in Example 1, which relates to the construction of hybridoma cell lines P1E4, P2E4 and P5C11. Each of these hybridoma cell lines was deposited and made part of the permanent stock culture collection of the American Type Culture Collection on Oct. 12, 1989. Hybridoma cell line P5C11 (LY-MB1) is available under the accession number ATCC HB 10262, while hybridoma cell line P1E4 (LY-MB2) is available under the accession number ATCC HB 10263. Hybridoma cell line P2E4 (LY-MB3) is available under the accession number ATCC HB 10264. Hybridoma cell line MF2:2.5A4 was prepared using the same general procedure disclosed in Example 1, except extracts of human coronary restenosis tissue was used as the initial immunogen. Hybridoma cell line MF2:2.5A4 secretes monoclonal antibody LY-MB5, an IgG2a antibody which also reacts with the MB001 antigen. Hybridoma cell line MF2:2.5A4 (LY-MB5) was deposited with the ATCC on Aug. 24, 1990 and is available under the accession number ATCC HB10535. Those skilled in the art will recognize that the antibodies of the present invention can be used in standard immunological reactions to isolate large amounts of MB001, which in turn can be used to create other hybridoma cell lines and monoclonal antibodies, all of which fall within the scope of the present invention.

The epitope(s) recognized by these monoclonal antibodies are naturally-occurring neoepitopes found on the atheroma-associated antigen, MB001. The epitope(s) may be modeled by modification of LDL by the storage of LDL in the absence of antioxidants, oxidation with iron, minimal oxidation by copper, conjugation with malondialdehyde or acetylation. The MB001 antigen is present in atherosclerotic lesions as demonstrated by antibody reactivity either by immunoperoxidase detection of antigen on frozen sections of lesions, or on Western blots of extracts prepared from atherosclerotic lesions with monoclonal antibodies produced by hybridoma cell lines P5C11, P1E4, P2E4 and MF2:2.5A4. The antigen is also found in the serum of the majority of individuals with documented coronary artery disease.

Antibodies of this invention can be utilized to purify the MB001 antigen from plasma, serum or tissue extracts. An affinity column matrix was constructed with antibody P5C11 for this purpose and standard affinity chromatography techniques were utilized to purify the MB001 antigen from plasma. Characterization of the affinity purified antigen preparation demonstrated the presence of human immunoglobulin. In addition, some human sera contain immunoglobulin species cross reactive with the MB001 antigen suggestive that humans can mount an immune response to the MB001 antigen. The measurement of this immune response could be of diagnostic/prognostic value to the study of peripheral or coronary artery disease.

The P2E4, P2E4, P5C11 and MF2:2.5A4 antibodies are merely illustrative of the invention, and all antibodies reactive with the MB001 neoepitope, regardless of species of origin or immunoglobulin class or subclass designation including IgG, IgA, IgM, IgE, and IgD are included in the scope of this invention. Monoclonal antibodies P1E4 and P2E4 have been found to be of the IgM class, while monoclonal antibody P5C11 is of class IgG2a. The present invention also provides antigen-binding fragments of the MB001-reactive antibodies. The ability to bind to the MB001 neoepitope is a general characteristic of antibodies of the invention.

As discussed above, antibodies of the invention can be constructed and isolated by immunization, preparation of hybridomas, and identification of antibodies with a reactivity to atherosclerotic lesions and normal tissue distribution similar to that of the disclosed MB001-reactive antibodies. However, the present invention also provides a means for identifying antibodies of the invention that does not require determination of antibody reactivity with a broad number of diseased and normal tissues. Antibodies of the invention can be identified by immunoreactivity and competitive binding studies using the MB001-reactive antibodies produced by the P1E4, P2E4 and P5C11 cell lines.

Similar migration patterns obtained when immunoblotting with the P5C11, P1E4 or P2E4 monoclonal antibodies can be used to identify antigenic determinants. Confirmation of identity can be obtained by depleting the antigen from tissue extracts or serum using excess amounts of one antibody and observing the inability of the other antibody to immunoprecipitate an antigen from the treated extract. Also, in instances where the antibodies bind to the same epitope or closely associated epitopes, each antibody will compete with the other for binding to the MB001 antigen. In this manner, other antibodies of the present invention can be identified.

Treatment of antibody preparations with proteolytic enzymes such as papain and pepsin generates antibody fragments, including the Fab and F(ab')2 species, which retain antigen-binding activity. Treatment of the antibodies of the invention with such enzymes can therefore be used to generate the MB001 binding fragments of the invention. The preparation of antigen binding fragments of the antibodies of the invention is illustrated in Example 8. Antigen-binding fragments of the MB001-reactive antibodies may be especially useful in therapeutic and diagnostic embodiments of the present invention.

Those skilled in the art will recognize that the antigen-binding region of the antibodies and antibody fragments of the invention is a key feature of the present invention. The MB001-reactive hybridoma cells of the invention serve as a preferred source of DNA that encodes one such antigen-binding region of the invention. This DNA, through recombinant DNA technology, can be attached to DNA that encodes any desired amino acid residue sequence to yield a novel "hybrid", or "chimeric" DNA sequence that encodes a hybrid, or chimeric, protein. In such a fashion, chimeric antibodies of the invention, in which one portion of the antibody is ultimately derived from one species and another portion of the antibody is derived from another species, can be obtained. Specifically, it may be desirable to replace the hypervariable (or complementary determining region) of a human antibody with the hypervariable region derived from a murine antibody with a desired antigenic specificity. The resulting "humanized" antibody would then more closely resemble a human antibody. The antigenic determinative region of the present antibodies can also be engineered into single chain or single domain protein molecules, therefore the present invention fully comprises any molecule that contains an MB001 antigen-binding region.

The antibodies of the present invention, can be used in immunological assays to diagnose the presence of the MB001 antigen in human tissue samples. Biopsy and necropsy samples of patients can be evaluated for the presence of atherosclerotic lesions using an MB001-reactive antibodies of this invention.

As modified LDLs are the progenitors of foam cell formation leading to atherosclerotic plaques, the ability to detect modified LDL in serum or plasma provides a diagnostic tool to assess plaque body burden, new plaque formation, to aid in risk assessment in asymptomatic patients or in the management of therapy.

A variety of formats for detection of the antigen in serum or plasma are readily apparent to the skilled artisan. For example, the serum and/or plasma can be assayed in solid phase where they are coated on an appropriate surface (such as in wells of an ELISA plate or on nitrocellulose paper or other support adequate for immunoassays). The presence of the antigen can be demonstrated directly using labelled antibodies or antibody fragments of this invention, or indirectly by first allowing the antibodies or fragments to bind, followed by detection of the presence of the antibodies using a variety of methods. The methods for antibody detection could include, but is not limited to, the use of monoclonal or polyclonal antibodies against mouse immunoglobulins or fragments, or labelled immunoglobulin binding species such as Protein A or Protein G.

The antigen may also be detected or purified using a capture assay where the antigen is captured from the serum or plasma using an antibody of this invention (to specifically capture modified LDL), or an antibody against native LDL (to capture all LDL). The captured antigen may then be detected directly or indirectly as described above. This type of assay can be performed in a number of formats using a variety of supports including ELISA plates, nitrocellulose or any other support material or matrix appropriate for immunoassays. Other techniques and devices useful for performing immunoassays are disclosed and claimed in U.S. Pat. No. 4,376,110, U.S. Pat. No. 4,632,901 and U.S. Pat. No. 4,727,019, the entire teachings of which are herein incorporated by reference.

Antibodies of the present invention can be labeled with detector groups including fluorescent labels, enzyme labels, and radioactive labels to identify lesions on the vessel wall or presence of the antigen in the serum. Detector groups used in the invention include fluorescein as a fluorescent label, peroxidase as an enzyme label and Iodine-125 as a radioactive label. Additional fluorescent labels which can be utilized in the invention include, but are not limited to, rhodamine, phycoerythrin and additional compounds emiting fluorescent energy. Additional enzyme labels which can be utilized in this invention include, but are not limited to, glucose oxidase and alkaline phosphatase.

Additional radioactive labels which can be utilized in this invention include, but are not limited to, Iodine 131 and Indium-111. These antibodies can also be labelled or conjugated with paramagnetic species and used in magnetic resonance imaging. Any of the following paramagnetic species may be used: species with unpaired electrons such as nitric oxide and nitrogen dioxide; ions containing unpaired electrons, such as elements in the transition metal series (including $Mn^{2+}$, $Mn^{3+}$, $Fe^{2+}$, $Fe^{3+}Ni^{2+}$, $Cr^{2+}$ and $Cu^{2+}$) or the Lanthamide series ($Gd^{3+}$ and $Eu^{2+}$); and stable free radicals such as nitroxides and triphenylmethyl. Antibodies can also be conjugated with spin labels, which are paramagnetic compounds based on unpaired electrons such as piperidine and pyrrolidine nitroxyl, and used for detection via electron spin resonance spectoscopy. One skilled in the art will clearly recognize that these labels set forth above are merely illustrative of the different labels that could be utilized in this invention. MB001 antigen-reactive antibodies can also be derivatized by conjugation to biotin and used, upon addition of species of avidins which have been rendered detectable by conjugation to fluorescent labels enzyme labels or radioactive labels in a multiplicity of immunochemical and immunohistological applications.

The antigen, hybridoma cell lines and monoclonal antibodies of the present invention are particularly useful because they provide methods for the diagnosis, prognosis and therapy of atherosclerotic disease. The antibodies may be specifically labeled so that atherosclerotic lesions can be imaged in vivo. As previously described, the preferred label would be a radionuclide, which could be directly conjugated to the antibody, or prepared as an antibody hybrid. Isotopes of elements such as indium, lead, rhenium, technicium, iodine, gallium, leutecium, astatine, bismuth, boron, platinum, silver, cobalt, yterbium, ruthenium, mercury, scandium, bromine, phosphorous and yttrium may be used to radioactively label antibodies of the invention.

The antibodies are also useful for immunotherapy, wherein the antibodies are conjugated to a cytotoxic or lesion destroying agent. Examples of such toxic agents are methotrexate, the vinca alkaloids or ricin. Other agents which could be linked to the antibodies of the present invention include antiinflammatory agents such as cyclosporin A or corticosteroids, growth factor antagonists such as suramin or angiopeptin, thrombolytics such as tissue plasminogen activator, cytokine inhibitors/agonists, antiotensin II antagonists such as saralasin and calcium channel blockers. A wide variety of linkage technologies are available, such as those disclosed in U.S. Pat. No. 4,845,200 and U.S. Pat. No. 4,801,688, the teachings of which are herein incorporated by reference. Radioisotopes such as those set forth above for lesion imaging can be used in therapeutic applications when attached to the MB001 antigen binding antibodies of the invention. The use of therapeutic agents consisting of MB001 antigen binding antibody-radioisotope immunoconjugates is therefore also contemplated in the present invention.

The antibodies of the present invention are also useful for the wide scale screening of individuals for the detection of coronary artery disease or risk thereof. As demonstrated in Example 3, the plasma or serum of a subject may be quickly and efficiently tested for the presence of the MB001 antigen. The antibodies may be incorporated into a screening kit, wherein the serum of a patient is immobilized, then contacted with a known quantity of MB001-reactive antibody, thereby allowing the quantification of the amount of MB001 antigen in the serum. Detection of the MB001 antigen in plasma or serum may not only provide a valuable patient diagnostic tool, but may also be important in drug screens for the evaluation of potential therapeutic modalities capable of inhibiting formation of oxidative or other modification of LDL in vitro and in vivo. Detection of the MB001 antigen may also be important in monitoring pharmaceutical efficacy effectiveness in patients (i.e., in therapy management). The general procedures followed in such an assay are provided in Example 1.

EXAMPLES

Examples provided are intended to assist in a further understanding of the invention. Particular materials employed, species and conditions are intended to be further illustrative of the invention and are not limiting upon the reasonable scope thereof.

EXAMPLE 1

Construction of MB001 Reactive Hybridoma Cell Lines

A. Antigen Preparation

Sections of human abdominal and thoracic aorta were obtained within 8 hours postmortem at autopsy. Tissue was placed in ice-cold Hank's Balanced Salt Solution (HBSS) containing 50 µg/ml gentamicin (Gibco, Inc., 2801 Industrial Drive, Madison, Wis. 53713). All buffers used through these preparations were ice-cold and all steps were performed with the tissue or homogenate chilled in an ice-bath or on an ice-pack. Vessels were opened longitudinally and grossly examined for atherosclerotic lesions. Four classifications of lesions were defined. Areas of the vessel wall that were slightly elevated and yellow were classified as fatty streak. Similar areas also exhibiting thin, slightly elevated lines of white fibrous tissue were defined as fatty streak/fibrous plaque. Fibrous plaque was defined as areas with frank lesions consisting of an elevated fibrous cap over a fatty or fibrous media. Lesions containing calcified or necrotic areas with or without surface thrombus were classified as advanced plaque. Areas containing different types of plaque were identified and carefully dissected apart. The adventitia was stripped away from the media and discarded. In some cases the intima and approximately the inner 30% of the media was stripped away from the outer media.

The intimal and inner medial tissue was weighed and then placed in sucrose extraction buffer (0.25M sucrose, 50 mM Tris, pH 7.4) containing a protease inhibitor cocktail (5 mM EGTA, 5 mM benzamidine, 1 mM phenyl methylsulfony fluoride, 10 µg/ml aprotinin, $2 \times 10^{-7}$M pepstatin and 10 mM N-ethylmalemide). The tissue was minced using scissors or a scalpel and then homogenized by six bursts (10 seconds each at setting 5) of a Polytron. Sucrose extraction buffer was added to the homogenate for a final concentration of 1 g tissue per 4 ml buffer. The homogenate was vortexed for 1 hour at 4° C. followed by centrifugation at 100,000×G for 1 hour at 4° C. The supernatant was removed and the pellet was resuspended in detergent extraction buffer (100 mM KCl, 100 mM LiBr, 25 mM $KPO_4$, 25 mM Tris, pH 7.4, 1% (w/v) CHAPS (Calbiochem, P.0. Box 12087, San Diego, Calif. 92112)) and protease inhibitor cocktail. The mixture was rehomogenized with two 10 second bursts of the Polytron, vortexed for 1 hour at 4° C. and centrifuged at 100,000×G for 1 hour at 4° C. The supernatant was collected and labeled "salt/detergent extract-diseased."

Extracts of disease-free vessel from younger individuals as well as from grossly normal areas of vessels adjacent to diseased areas were prepared in substantial accordance with the above teaching and were labeled "salt/detergent extract-normal." All extracts were stored at −80° C.

B. Immunization

The methodology for monoclonal antibody production was introduced by Kohler and Milstein, Nature 495 (1975) and is now well established in the art. A more recent review by Gaflre and Milstein in "Methods in Enzymology" Vol. 73, Langone and Vunakis, ed., p. 3-46 (Academic Press, New York, 1981) summarizes improvements of the original method, provides detail on needed equipment and reagents, and describes in detail the steps, to produce the monoclonal antibodies. A pool of salt-detergent extracts from diseased tissue was prepared by combining 2 mg from each of seven extracts derived from four individuals as listed in Table 1.

TABLE I

| Donor | Type of Lesion |
| --- | --- |
| 1 | Abdominal aorta advanced fibrous plaque |
| 1 | Abdominal aorta fibrous plaque |
| 2 | Abdominal aorta fibrous plaque |
| 2 | Thoracic aorta fibrous plaque |
| 3 | Abdominal aorta fibrous plaque |
| 4 | Abdominal aorta fibrous plaque |
| 4 | Abdominal aorta advanced fibrous plaque |

Immunogen was prepared by emulsifying the pooled salt-detergent extract with complete Freund's adjuvant (1:1) for a final concentration of 228 μg/ml. Both hind footpads of five young adult Balb/C mice were injected with 100 μl of immunogen each. On the third and seventh day following the initial injection the hind footpads were injected with 100 μl of the same antigen prepared in incomplete Freund's adjuvant. Mice are illustrative of the method; skilled artisans realize that there are no limitations as to the species used as a source of immune cells. Other species, including humans, rats, and hamsters are known to be useful, while in theory any species including rabbit, goat, sheep, pig, chicken and monkey could be useful. Other routes of injection, or the use of the spleen as the initial inoculant, could also be used to create hybridomas of the present invention.

C. Preparation of Lymph Cells

On the tenth day following the initial injection the immunized mice were sacrificed by ether suffocation followed by exsanguination. The popliteal lymph nodes from both hind legs of each mouse were aseptically removed, then crushed with the plunger of a 10 ml syringe to release the lymph node cells.

D. Preparation of Myeloma Cells

HL-1 TM Friendly myeloma-653 cells (Ventrex Laboratories, P.O. Box 9701, Portland, Me. 04013) were selected for use as a fusion partner for the atheroma associated antigen reactive lymphocyte preparation. These cells were obtained from Ventrex and maintained as per supplier's instructions. Two days prior to fusion, myeloma cells were transferred into 75 cm² tissue culture flasks to assure log phase growth which is important for successful hybridoma generation.

Although HL-1 TM Friendly 653 cells are the preferred myeloma for cell-fusion, conventional mouse-derived established myeloma cell lines, including P3-X63-Ag8-U1 (P3U1), SP2/0-Ag14 (SP-2), P3-X63-Ag8-6.5.3 (X63.6.5.3), p3-X63-Ag8 (X63), P3-NS-1-Ag4 (NS-1), MPC11-45.6 TGI.7 (MPC-11), and S194/5XXO.BU1 (S194) (see Gaflre and Milstein, 1981, in "Methods in Enzymology" Vol. 73B, Langone and Van Vunakis, ed.) can also be used for purposes of the present invention.

E. Cell Fusion

Lymphocytes and myeloma cells were washed by centrifugation at 200 g for 5 minutes at 4° C., followed by aspiration of supernate and resuspension of cells in DME (Gibco). After 3 DME wash steps, the cells were enumerated and viability was simultaneously evaluated by trypan blue exclusion. As used herein, cell numbers refer only to viable cells (those not stained with trypan blue). $1.5 \times 10^7$ myeloma cells were added to $3.0 \times 10^7$ lymphocytes in a 50 cc centrifuge tube. The cells were centrifuged at 800 g for 5 minutes at 4° C., and the supernate was aspirated as completely as possible without loss of cells from the pellet. The cell pellet was then loosened by gently tapping the tube. 1.5 mls of fusing media (formulation below) at 37° C. were added, the contents gently agitated, and the tube left undisturbed for 30 seconds. DME which was warmed to 37° C., was then added dropwise with gentle agitation to slowly bring the contents to a volume of 20 ml. An additional 30 ml of 37° C. DME was added. Caution must be exercised while diluting the mixture to avoid breaking up the cell aggregates. The fusion was centrifuged at 200 g for 5 minutes and gently resuspended into 60 ml of HL-1 TM culture media (Ventrex) containing 20% fetal bovine serum (Gibco) and 1X HAT.

HAT is a mixture of hypoxanthine, aminopterin, and thymidine used to select for splenocyte/myeloma hybrids. Formulations of HAT and PEG 4000 (fusing media) preparation are provided below.

| HAT (100X) | Amt./25 ml. |
| --- | --- |
| Hypoxanthine (1000 uM) | 34 mg |
| Aminopterin (100 uM) | 11 mg |
| Thymidine (300 uM) | 18.25 mg |

To prepare, dissolve separately in 1 to 5 drops of 1N NaOH, mix together, rinse tubes and bring up to 25 ml in DME. HAT is diluted 1:100 in culture media at time of use. HAT is also commercially available from Gibco.

Fusing Medium can be prepared as follows. Autoclave 20 gm PEG 4000 (J. T. Baker Chemical Co., 222 Red School Lane, Phillipsburg, N.J. 08865) in a 100 ml bottle. Add 28 ml sterile Dulbecco's PBS (Gibco) containing 15% DMSO, mix and store at 4° C.

F. Preparation of Feeder Cells 10 ml of ice cold DME was injected into the peritoneal cavity of a BALB/C mouse using an 18 gauge needle. The peritoneal cavity was agitated and the peritoneal wash was removed. The peritoneal cells were placed in an ice cold centrifuge tube and centrifuged at 250 g for 5 minutes. Following supernate aspiration, the cells were resuspended in 2 ml of ice cold HL-1 medium (Ventrex) and placed on ice.

G. Tissue Culture of the Hybridomas

The feeder cells (peritoneal lavaged cells) were combined with the cell fusion mixture and mixed. One hundred microliters per well of the cell mixture were added to 96 well tissue culture plates. A humidified 37° C. incubator with an atmosphere at 5% $CO_2$ was used to maintain the cell-fusion products. The volume of all wells was increased to 200 ul with HL-1 (Ventrex) containing 20% fetal bovine serum (Gibco) and 1X HAT on day seven.

H. Selection of Antigen Specific Hybridomas

When macroscopic clones became apparent in the 96 well plates, 110 μl aliquots were removed and evaluated for antigen reactivity using a standard enzyme-linked immuno-adsorbent assay (ELISA). Two sets of antigen plates were prepared; one set contained "diseased" extract and one set contained "normal" extract. One hundred microliters of coating solution (25 μg/ml disease extract or 25 μg/ml normal extract diluted in 0.1M carbonate/bicarbonate, pH 9.6) were added per well of a 96 well titer plate. The plates were incubated overnight at 4° C., then the antigen solution was removed and the wells were filled with 200 μl blocking solution (10% calf serum in Phosphate Buffered Saline (PBS), pH 7.2). The plates were incubated for one hour at room temperature (about 22° C.), then the wells were emptied and washed three times with 300 μl of washing buffer (PBS, pH 7.2, containing 0.2% Tween 20). Each antibody solution was assayed against both normal and diseased extract. The plates were filled with 50 μl/well of the antibody solution drawn from the hybridoma cells and incubated for 1.5 hours at 37° C. in a 5% $CO_2$ incubator. Fifty μl of the antibody solution drawn from the hybridoma cells were placed in wells coated with salt/detergent extract-"diseased" and 50 μl were placed in wells coated with salt/detergent extract-"normal". Following incubation, the plates were emptied and each well wash washed three times with 300 μl of washing buffer.

The secondary antibody used to complete the ELISA was an affinity isolated Goat anti-mouse IgG and IgM/-horseradish peroxidase conjugate adsorbed to remove cross reactivity to human serum proteins. This antibody was purchased from TAGO, Inc., (887 Mitten Rd., P.O. Box 4463, Burlingame, Calif. 94011) and was added at a 1:1000 dilution in dilution buffer (washing Buffer with BSA at 1 mg/ml) at 50 μl/well. The plates were incubated for 1 hour at room temperature, then washed five times with wash buffer. Substrate solution (4 mM ortho-phenyleneaminediamine (Sigma) and 0.004% (v/v) $H_2O_2$ in citric acid/phosphate buffer, pH 5.0) was added at 50 μl per well and the plates were allowed to incubate for 5-10 minutes at room temperature. Next, 25 μl of 4N $H_2SO_4$ was added to each well to terminate the peroxidase reaction. The ELISA plates were then loaded onto an ELISA plate reader and the optical densities were determined with wavelength settings of 490 nm/570 nm. The Reader was blanked against a row of wells which contained no antigen extract.

I. Cloning and Isotyping

Three hybridoma cell lines were found which produce antibody reactive with the disease extract but not the normal extract. These hybridoma cell lines were designated P1E4, P2E4 and P5C11. Each of the three hybridoma cell lines were cloned using a Coulter ™ (Coulter Electronics, Hialeh, Fla.) autocloner to ensure the monoclonability of each of the hybridoma cell lines. The general method for cloning is disclosed in U.S. patent application Ser. No. 07/400,643, filed Aug. 30, 1989, the entire teaching of which is herein incorporated by reference.

A murine monoclonal sub-isotyping kit obtained from HyClone Laboratories and instructions provided by the vendor were used to determine the isotype of the antibodies produced by the cell lines. Monoclonal antibodies produced by hybridoma cell lines P1E4 and P2E4 were shown to be IgM type antibodies, while the antibodies produced by hybridoma cell line P5C11 was shown to be type IgG2a.

These three hybridoma cell lines were deposited with and made part of the permanent stock culture collection at the American Type Culture Collection (ATCC) in Bethesda, Md. on Oct. 12, 1989. A culture of hybridoma cell line P5C11 (LY-MB1) can be obtained from the ATCC under the accession number ATCC HB 10262, and a culture of hybridoma cell line P1E4 (LY-MB2) can be obtained under the accession number ATCC HB 10263. A culture of hybridoma cell line P2E4 (LY-MB3) can be obtained from the ATCC under the accession number ATCC HB 10264.

EXAMPLE 2

Production of P1E4, P2E4 and P5C11 Antibodies

Vials of frozen P1E4 (LY-MB1), P2E4 (LY-MB2) and P5C11 (LY-MB3) hybridomas can be obtained from the American Type Culture Collection, Rockville, Md., under the accession number ATCC HB 10262, ATCC HB 10263 and ATCC HB 10264, respectively. Viable cells are recovered by thawing vial contents in a 37° C. water bath while swirling the vial to facilitate rapid and uniform thawing. The cell suspension is diluted 1:2 with Balanced Salt Solution (BSS-Gibco) and centrifuged at 200 g through a serum underlay to partition the cells from cryogenic media. Following aspiration of material above the cell pellet, cells are harvested, diluted in tissue culture media supplemented with serum and antibiotics as is common in the art and established in cell culture under standard conditions (37° C. and 5% $CO_2$). Normally, Ventrex HL-1 ™ media supplemented with 10% Fetal Bovine Serum (Gibco) and 50 μg/ml gentamycin (Gibco) was used for all hybridomas of the present invention, although occasionally media without antibiotic was used. During cell culture, it is advisable to maintain the cells at concentrations of $1 \times 10^5 - 7 \times 10^5$ cells/ml although modest variances are well tolerated.

The respective antibodies may be recovered from tissue culture in μg/ml quantities. Alternatively, antibody production may be more productively pursued by establishing the hybridomas as ascites tumors in rodent species. Antibody production and harvesting methods are detailed in an excellent review by Gaflre and Milstein in "Methods in Enzymology", 1981, Vol. 73B, Langone and Van Vunakis, et., p. 43-45 (Academic Press, New York), the entire teaching of which is herein incorporated by reference.

EXAMPLE 3

Determination of Antibody Binding to the Antigen of the Present Invention

A pool of human plasma from five donors, along with a fresh preparation peripheral blood leukocytes, was screened with the supernatants of hybridoma cell lines P1E4, P2E4 and P5C11 in substantial accordance with the teaching of Example 1H. None of the supernatants reacted with peripheral blood leukocytes, however, the three supernatants reacted with the pooled plasma. Plasma from the five donors were screened individually and each of the supernatants reacted with only one plasma sample, from a donor with elevated serum cholesterol and triglycerides.

To further investigate the serum reactivity of the antibodies, the serum and/or plasma from a larger pool of patients was assayed. The donor pool included thirty-two patients with angiographically documented coronary artery disease, twenty-nine symptom-free, presumed normal subjects and six symptom-free, presumed normal subjects with medically recognized coronary artery disease risk factors. The tests were performed by solid phase ELISA in substantial accordance with the teaching of Example 1H. The data collected is summarized in FIG. 1 of the accompanying drawings.

EXAMPLE 4

MB001 Antigen Characterization

To establish the identity of the MB001 antigen recognized by monoclonal antibodies P5C11 (LY-MB1), P1E4 (LY-MB2) and P2E4 (LY-MB3), native LDL and LDL modified by a variety of methods (described in subsequent Examples) were tested for antibody reactivity. Antigen plates were prepared from the LDL preparations and standard solid phase ELISAs were performed in substantial accordance with the teaching of Example 1H. The results are summarized in Table II.

TABLE II

| Antigen | Antibody Reactivity |
| --- | --- |
| Native LDL stored in 1 mM BHT | − |
| Native LDL stored under $N_2$ (g) | − |
| Native LDL not protected from oxidation | + |
| LDL conjugated with malondialdehyde | + |
| Acetylated LDL | + |
| Iron oxidized LDL (mild oxidation) | + |
| LDL minimally oxidized with copper | + |
| LDL extensively oxidized with copper | − |

To establish the nature of the MB001 antigen recognized by the P1E4 (LY-MB2), P2E4 (LY-MB3) and P5C11 (LY-MB1) antibodies, a sample of human serum shown to react with the antibodies was subjected to various treatments commonly known to the skilled artisan. Antigen plates were prepared from the treated serum and standard solid phase ELISAs were performed in substantial accordance with the teaching of Example 1H. The results are summarized in Table III.

TABLE III

| Treatment | Antibody Reactivity |
| --- | --- |
| 1. Held at 56° C. for 45 minutes | + |
| 2. Held at 80° C. for 30 minutes | − |
| 3. Limited pepsin digestion | decreased |
| 4. Neuraminidase treatment | increased |
| 5. Limited trypsin digestion | decreased |

The samples of salt/detergent extract from diseased tissue as well as serum from donor 8 (a known positively reacting serum) were separated according to molecular weight by standard electrophoresis on 5% SDS polyacrylamide gels. Samples were prepared in standard SDS electrophoresis sample buffer (both with and without a reducing agent) but samples were not boiled, but were heated to 56° C. for 5 minutes. After electrophoresis, the gels were blotted onto nitrocellulose and strips of the blots were probed with monoclonal antibodies 9.2.27 (anti-chondroitin sulfate glycoprotein), KS1/4 (anti-adenocarcinoma antigen), HFF-37 (anti-smooth muscle alpha actin), 3E1 (anti-fibronectin), P1E4, P2E4 and P5C11. These immunoblots were carried out according to standard Western blot techniques. Following several washes, the blots were probed with peroxidase labeled anti-murine Ig antibodies and were developed with 4-chloro-1-napthol (KPL). All three of the antibodies of the present invention recognized what appeared to be a pair of identical bands on the non-reduced gel blots of both the serum and tissue extracts. Both bands are of apparent molecular weight of greater than 220,000 daltons. Antibodies P1E4, P2E4 and P5C11 did not show any reactivity on blots from reduced gels.

The MB001 antigen recognized by antibodies P1E4, P2E4 and P5C11 was partially purified from human serum by gel filtration on a Pharmacia Superose 12 TM column using a Pharmacia FPLC System in accordance with the manufacturer's suggested protocols. The results indicated that the MB001 antigen is found in the fractions containing the species with the largest molecular weight. Similar results were seen with the Pharmacia Superose 6 TM column, which is recommended for higher molecular weight separations. The antigen can be further purified by standard capture assay techniques or by standard immunopurification techniques such as immuno-affinity chromatography.

EXAMPLE 5

Immunohistology

Frozen sections from thoracic and abdominal aortas and from coronary arteries were cut and incubated with spent media from hybridoma cell lines P1E4, P2E4 and P5C11, as well as with control IgG and IgM antibodies (at 10 μg/ml). The slides were washed several times then incubated with biotin labeled goat anti-mouse IgG+M antibody followed by peroxidase labeled streptavidin. The presence of the monoclonal antibody/peroxidase complexes were localized with 3-3'-diaminobenzamidine (Sigma) according to standard techniques. Each of the three antibodies (P1E4, P2E4 and P5C11) demonstrated similar staining patterns on all sections stained. Reactivity was noted only in lesions and was not observed in normal areas of the vessel wall surrounding the lesion.

EXAMPLE 6

Production of Polyclonal Antibodies Reactive with the MB001 Antigen

Production of conventional antisera to both soluble and particulate (cellular) antigens are well established in the art. Polyclonal antibody production follows injection of foreign matters into any immunologically competent vertebrate species. Ideally, animals serving as producers of the antisera are challenged with antigen repetitively until optimal humoral responsiveness, as measured after trial bleedings, is attained. Any MB001 antigen positive material is appropriate for immunization purposes. For the best results, the antigen should be purified as described in Example 5, then further purified by passing the solution through an immuno-affinity column prepared by standard procedures using any of the monoclonal antibodies of the present invention. Reactivity of the resulting antisera towards the MB001 antigen can be determined as taught in Example 1H.

EXAMPLE 7

Conjugation of Detector Groups to Antibodies of the Invention

The method taught in Example 5 is readily modified to eliminate the need for the second antibody (biotinylated goat anti-mouse Ig) by directly biotinylating the specific MB001-reactive antibody. The preferred antibody is purified using Protein A chromatography, desalted into 0.1M NaHCO$_3$, then adjusted to pH 8.5–8.6 with 0.1M NaHCO$_3$ by dialysis or Sephadex G25 ® (Sigma). Prepared columns of G25 are commercially available from Pharmacia Chemical Co. as PD10 ® columns. MB001-reactive antibodies are adjusted to a concentration of 1 mg/ml in 0.1M NaHCO$_3$, pH 8.5–8.6. N-hydroxysuccinimidobiotin (Pierce Chemical Co., P.O. Box 117, Rockford, Ill. 61105) is rapidly dissolved into DMSO at a concentration of 1 mg/ml, and 120 µl of MB001-reactive antibody is added and mixed immediately. The reaction mixture is left at room temperature for 4 hours. The conjugated antibody is separated from unreacted N-hydroxysuccinimidobiotin by either dialysis or passage through Sephadex G25 ®. Detection is facilitated upon reaction of biotinylated MB001-reactive antibody with avidin conjugates of fluorescent moieties, radioactive species, or enzymes. The use of avidin-biotin systems of detection is widely exploited in the art and the aforementioned avidin conjugates are commercially available through numerous vendors.

Attachment of fluorescent labels directly to antibodies of the invention can be accomplished by methods set forth in "Selected Methods in Cellular Immunology", 1980, Mishell and Shiigi, ed., Freeman and Company, San Francisco p. 292–302, and the teaching of which is herein incorporated by reference.

EXAMPLE 8

Preparation of P5C11 antigen binding fragments

The F(ab')$_2$ fragment of antibody P5C11 is prepared by adding 2.4 ml of pepsin solution, containing 12.6 mg of pepsin/ml, to 1.5 g of P5C11 antibody in 270 ml of physiological buffered saline. The mixture is held at 37° C for 2 hours, and then the reaction is stopped by the addition of triethanolamine. The product is then purified by chromatography on a Sepharose Fast Flow column, eluting with 0.15M sodium acetate. The F(ab')$_2$-containing fractions are combined and concentrated by dialysis. Fab fragments are prepared in an analogous manner except papain is used, rather than pepsin.

EXAMPLE 9

Reaction of Antibodies with Chemically-Modified LDL

A. MDA oxidation and Thiobarbituric Acid Assay

The protein (LDL, Biomedical Technologies, Inc. 378 Page St., Stoughton Mass. 02072) was dialyzed against four 1 liter aliquots of Buffer A 0.01M sodium phosphate, dibasic (5.68 g/4 liters), pH=7.4, 0.15M NaCl (35.129 g/4 liters) and 0.01% EDTA (0.4 g/4 liters)] for 30 minutes each. Malondialdehyde-bis-(dimethylacetal) (0.33 ml; Aldrich Chemical Co.) was mixed with 0.4 ml of concentrated hydrochloric acid in a 25 ml scintillation vial. After 2 minutes, 10 ml of buffer B (0.1M sodium phosphate, monobasic (1.38 g/100 ml), pH 6.4) was added and the pH was adjusted to 6.4 ml with 5 N NaOH. The protein solution was added (5 mg of LDL in 1 ml of buffer A) and the reaction mixture is left at room temperature. The pH of the reaction mixture was checked occasionally to see that the pH remained at 7.0.

At time point zero (immediately after addition of the protein) and at 15 minutes, 30 minutes, 1, 2, and 4 hours a 0.050 ml aliquot was removed for a time study assay. These aliquots were quenched by mixing with an equal volume of 3M glycine and placed on ice. After 4 hours the entire remaining sample was dialyzed overnight against three changes of buffer A (1 liter each).

MDA-conjugated LDL was sterilized by filtering through a 0.22 µnylon filtering unit (Millipore) and stored at 4° C. Malondialdialdehyde (MDA) is a product of peroxidation and is commonly used as a measure of the extent of oxidation. MDA is measured by first allowing it to react with thiobarbituric acid which gives a red species which is measured spectrophotometrically.

LDL was modified as described previously, diluted to 0.1 to 2.0 mg of protein per ml in PBS containing 1 mM BHT or 5 mM EDTA and 100 µl of this suspension was mixed with 0.75 ml of a solution containing trichloroacetic acid (15% w/v); thiobarbituric acid (0.375% w/v) and hydrochloric acid (0.25N; TCA-TBA-HCL). The mixture was heated for 15 minutes in a boiling water bath. After cooling, the flocculent precipitate was removed by centrifugation at 1000×G for 2 minutes and the absorbance of the supernatant was determined at 535 nm against a blank containing PBS and TCA-TBA-HCL. The malondialdehyde concentration of the sample can be calculated using an extinction coefficient of $1.56 \times 10^5$ M$^{-1}$ cm$^{-1}$. Alternatively, the malondialdehyde concentration of the sample may be determined using a standard curve constructed by reacting a range of known concentrations of malonaldehyde (bis)dimethylacetal in the TBARS assay and plotting the absorbance readings versus the known concentrations.

B. Copper Oxidation and Iron Oxidation

LDL was oxidatively modified by incubating 100 µg/ml of LDL in HBSS containing copper (0.2–5.0 µM) or iron (1 µM) in a volume of 0.5 ml at 37° C. for 24 hours. The reaction was terminated by the addition of EDTA for a final concentration of 1.0 mM. LDL was also oxidatively modified by incubation of 10 µg/ml in Ham's F-10 medium (GIBCO) with confluent human muscle cells or endothelial cells for 24 hours at 37° C.

C. Acetylated LDL

Acetylated LDL was purchased from BTI (same address as above) and stored in 1 mM BHT.

D. Minimal Oxidation by Copper

LDL was oxidized by a range of copper concentrations and the extent of oxidation was measured by the amount of thiobarbituric acid reactive substances (TBARS) generated, the standard assay for such determinations. The reactivity of the P5C11 (LY-MB1) monoclonal antibody of this invention with LDL oxidized to various extents by copper was evaluated in the standard solid phase ELISA and the reactivity (OD) vs the concentration of TBARS present in the ox-LDL is shown in FIG. 3. The antibody is reactive with minimally oxidized LDL; however, upon extensive oxidation, the epitope is destroyed.

E. Results

The antibodies of the present invention were next allowed to react with the chemically-modified LDL molecules produced above. The assays were performed in substantial accordance with the teaching of Example 1H. The antibodies displayed reactivity with the MDA-LDL molecules as shown in FIG. 3 of the accompanying drawings. The results of the reactivity studies with the rest of the chemically-modified LDL molecules are summarized in Table II.

EXAMPLE 10

Competition Assay

Biotin was conjugated to LY-MB1 and the ability of P5C11 (LY-MB1), P1E4 (LY-MB2) and P2E4 (LY-MB3) to compete with the biotinylated LY-MB-1 for binding to the antigen was analyzed by solid phase ELISA. Equal volumes of a standard concentration of biotinylated LY-MB1 (2 $\mu$g/ml) and a series of dilutions of each competing antibody (spent medium from hybridoma cultures diluted in PBS from 1:1 to 1:100) were mixed and the binding of the biotinylated LY-MB1 was evaluated via the standard ELISA using peroxidase-labelled Streptavidin (TAGO; at 1:100 dilution). FIG. 4 illustrates that each monoclonal antibody was capable of competing with biotinylated LY-MB-1 indicating that the antibodies may bind to the same or closely apposed epitopes on modified LDL such that they interfere with each others binding or that binding of one antibody causes a conformational change resulting in destruction of the epitope recognized by the labelled antibody.

EXAMPLE 11

Capture Assay

Purified monoclonal antibody P5C11 (LY-MB1) was bound to an ELISA plate in substantial accordance with the teaching of Example 1H, at a concentration of 10 $\mu$g/ml. Buffer was added to each well containing various dilutions of plasma containing the MB001 antigen. Plasma previously shown to not contain the antigen was added to some wells as a negative control. After binding, the wells were washed and a 1 $\mu$g/ml biotinylated P5C11 (LY-MB1) antibody solution was added. After binding of this antibody to the captured antigen, the wells were again washed and the OD of the reactants was measured. The results of this experiment are presented in FIG. 5 of the accompanying drawings.

EXAMPLE 12

Affinity Chromatography

An LYMB-1 sepharose affinity column was prepared by reacting LYMB-1 (30 mg of purified protein) with CNBr-activated sepharose 4B (Pharmacia) following the manufacturers directions. Serum, previously identified to be LYMB-1 positive by solid-phase ELISA screening, was diluted with PBS and loaded onto the column. The column was then washed with phosphate buffered saline (PBS), ph 7.4, until the optical density (O.D.) readings at 280 nM of the flow through solution reached background levels. The column was then eluted with 0.1M glycine pH 3.5. Fractions were collected into tris-HCl (pH 8.0) to neutralize the glycine.

Subsequent experiments involved an immunological analyses of the flow through and affinity isolated components recognized by monoclonal antibody LYMB-1. The amount of LYMB-1 positive low density lipoprotein in the starting material (the epitope is consistent with minimally modified low density lipoprotein) and flow through were compared by first diluting each such that they were at the same final dilution. For example, 2.5 ml of platelet poor plasma was injected and 40 ml of flow through material was subsequently collected from the affinity column fractions; thus the flow through material is a 1:15 dilution of the original platelet poor plasma. Starting material was diluted 1:500 and flow through was diluted 1:33, each in diluting buffer. The eluted fractions were diluted 1:200 in coating buffer. Samples were plated in ELISA plates and assayed according to the standard solid phase serum ELISA in substantial accordance with the teaching of Example 1. No LYMB-1 reactivity was detected in the flow through material while the starting material remained positive. This result demonstrates that the monoclonal antibody effected complete immunodepletion of modified LDL epitope containing molecules from the plasma. The glycine elution peak contained all reactivity with LYMB-1 in fractions 16 through 30 from the affinity column. These results indicate that LYMB-1 can be used to purify LYMB-1 epitope positive macromolecules from human plasma and that antigen-depleted serum can be obtained (i.e. the flow through material which is completely depleted of reactivity below the sensitivity of the standard solid phase serum ELISA).

Flow through samples and glycine-elution fractions from the above experiment were also coordinately analyzed using a capture ELISA assay: monoclonal anti-native LDL antibody (Medix Biotech Institute, Foster City, Calif. 94404) was diluted to 10 $\mu$g/ml in coating buffer and allowed to adsorb to ELISA plates overnight. Serum, flow through material from the column or glycine elution fractions were diluted in PBS and added to wells for the capture step. Wells were washed and the captured material was measured using biotynylated LYMB-1. The results of these experiments again demonstrated that the glycine-elution fractions contained all of the LYMB-1 epitopes (consistent with minimally modified LDL) while the flow through fractions were depleted for LYMB-1 epitopes but did contain non-modified molecules.

EXAMPLE 13

Cross-Depletion

The molecular weight profiles observed on "Western" immunoblots of plasma using the LY-MB1 antibody demonstrate that the LY-MB1 antibody reacts with several molecular species that migrate to the same position as native LDL. Significant reactivity is also observed in several higher molecular weight components on these blots. Purified LDL from a variety of donors was run on 5% SDS-polyacrylamide gels and blotted onto nitrocellulose. Identical blots were probed with monoclonal antibody LY-MB1, monoclonal anti-Lp(a) antibody (Cappel, Organon Teknika Corp., West Chester, Pa. 19380) or anti-native LDL antibody (Medix, Inc.). The reactivity of LY-MB1 and anti-Lp(a) were identical on each sample tested.

LY-MB1-positive (minimally-modified) LDL was purified on the LY-MB1 affinity column in substantial accordance with the teaching of Example 12. Starting material, flow through and fractions were placed in solid phase as previously described and assayed for LY-MB1 antigen, Lp(a) and native LDL using the standard solid phase serum ELISA. Both starting material and flow through contained native LDL while flow through was depleted of both the LY-MB1 antigen and Lp(a), thereby demonstrating that I Y-MB1 can capture Lp(a). The reactivity profile of the fractions was identical for the LY-MB1 (MB001) antigen and Lp(a).

A capture assay was also performed where Lp(a) antibody was absorbed to a plate and was able to capture LY-MB1 reactive material. In addition, using the standard solid phase serum ELISA, the Lp(a) and LY-MB1 reactivities were measured and a 1:1 relationship between the two was discovered.

We claim:

1. A method for preparing an MB001 atheroma-associated immunogen, said method comprising the steps of:
   a) homogenizing human plaque intimal and inner medial tissue in a sucrose extraction buffer to create an initial homogenate,
   b) centrifuging said initial homogenate to precipitate any insoluble homogenate,
   c) removing the supernatant from the insoluble homogenate,
   d) solubilizing said sucrose-insoluble homogenate in a detergent extraction buffer containing lithium bromide.

2. A method for preparing an antibody reactive with the MB001 atheroma-associated antigen, said method comprising:
   a) homogenizing human plaque intimal and inner medial tissue in a sucrose extraction buffer to create an initial homogenate,
   b) centrifuging said initial homogenate to precipitate any insoluble homogenate,
   c) removing the supernatant from the insoluble homogenate,
   d) solubilizing said sucrose-insoluble homogenate in a detergent extraction buffer containing lithium bromide,
   e) immunizing a suitable non-human mammal with said detergent extract, then
   f) preparing antibody-secreting hybridoma cells from the tissue of said immunized non-human mammal.

3. The method of claim 2 wherein said suitable human mammal is a mouse.

4. The method of claim 3 wherein said mouse is a Balb/c mouse.

* * * * *

UNITED STATES PATENT AND TRADEMARK OFFICE
CERTIFICATE OF CORRECTION

PATENT NO.    : 5,196,324

DATED         : March 23, 1993

INVENTOR(S)   : Thomas F. Bumol et al.

It is certified that an error appears in the above-identified patent and that said Letters Patent is hereby corrected as shown below:

Column 20, line 21, "human" should read, -- nonhuman --.

Signed and Sealed this

Seventeenth Day of October, 1995

Attest:

BRUCE LEHMAN

*Attesting Officer*              *Commissioner of Patents and Trademarks*